US009090837B2

(12) United States Patent
Subramaniyam

(10) Patent No.: US 9,090,837 B2
(45) Date of Patent: *Jul. 28, 2015

(54) HIGH TEMPERATURE NAPHTHENIC ACID CORROSION INHIBITION USING ORGANOPHOSPHOROUS SULPHUR COMPOUNDS AND COMBINATIONS THEREOF

(75) Inventor: Mahesh Subramaniyam, Mumbai (IN)

(73) Assignee: DORF KETAL CHEMICALS (I) PRIVATE LIMITED, Munbai (IN)

( * ) Notice: Subject to any disclaimer, the term of this patent is extended or adjusted under 35 U.S.C. 154(b) by 534 days.

This patent is subject to a terminal disclaimer.

(21) Appl. No.: 12/593,622

(22) PCT Filed: Mar. 27, 2008

(86) PCT No.: PCT/IN2008/000195
§ 371 (c)(1),
(2), (4) Date: Sep. 29, 2009

(87) PCT Pub. No.: WO2008/120236
PCT Pub. Date: Oct. 9, 2008

(65) Prior Publication Data
US 2010/0126842 A1    May 27, 2010

(30) Foreign Application Priority Data

Mar. 30, 2007 (IN) .......................... 604/MUM/2007

(51) Int. Cl.
*C10G 75/02* (2006.01)
*C07F 9/04* (2006.01)
(52) U.S. Cl.
CPC .. *C10G 75/02* (2013.01); *C07F 9/04* (2013.01)
(58) Field of Classification Search
CPC .................................. C10G 75/02; C07F 9/04
USPC .............. 208/47, 348–349; 203/7; 568/13–14
See application file for complete search history.

(56) References Cited

U.S. PATENT DOCUMENTS

| | | | |
|---|---|---|---|
| 1,872,091 A | 8/1932 | Mougey | |
| 2,316,078 A * | 4/1943 | Gaynor et al. | 508/354 |
| 2,316,087 A * | 4/1943 | Gaynor et al. | 508/325 |
| 2,688,612 A | 9/1954 | Watson | |
| 2,915,517 A | 12/1959 | Le Suer | |
| 3,132,975 A | 5/1964 | Freud | |
| 3,145,886 A | 8/1964 | Goodwin | |
| 3,201,438 A | 8/1965 | Reed | |
| 3,260,622 A | 7/1966 | Le Suer | |
| 3,281,359 A | 10/1966 | Oberender et al. | |
| 3,324,032 A | 6/1967 | O'Halloran | |
| 3,428,561 A | 2/1969 | Lesuer | |
| 3,459,662 A | 8/1969 | Hu | |
| 3,460,989 A | 8/1969 | Rusch | |
| 3,489,682 A | 1/1970 | Lesuer | |
| 3,531,394 A | 9/1970 | Koszman | |
| 3,668,237 A | 6/1972 | Cyba | |
| 3,909,447 A | 9/1975 | Redmore et al. | |
| 4,024,049 A | 5/1977 | Shell et al. | |
| 4,024,050 A | 5/1977 | Shell et al. | |
| 4,105,540 A | 8/1978 | Weinland | |
| 4,443,609 A | 4/1984 | Oude Alink et al. | |
| 4,542,253 A | 9/1985 | Kaplan et al. | |
| 4,578,178 A | 3/1986 | Forester | |
| 4,600,518 A | 7/1986 | Ries et al. | |
| 4,842,716 A | 6/1989 | Kaplan et al. | |
| 4,906,391 A | 3/1990 | Andress | |
| 4,927,561 A | 5/1990 | Forester | |
| 4,941,994 A | 7/1990 | Zetlmeisl et al. | |
| 5,182,013 A | 1/1993 | Petersen et al. | |
| 5,252,254 A | 10/1993 | Babaian-Kibala | |
| 5,314,643 A | 5/1994 | Edmondson et al. | |
| 5,484,542 A | 1/1996 | Cahoon et al. | |
| 5,500,107 A | 3/1996 | Edmondson | |
| 5,552,085 A | 9/1996 | Babaian-Kibala | |
| 5,611,991 A | 3/1997 | Naraghi | |
| 5,630,964 A | 5/1997 | Babaian-Kibala et al. | |
| 5,725,611 A | 3/1998 | Wright et al. | |
| 5,863,415 A | 1/1999 | Zetlmeisl | |
| 6,512,133 B1 | 1/2003 | Götzmann et al. | |

(Continued)

FOREIGN PATENT DOCUMENTS

EP    0 565285 B1    5/1997
EP    1063276 A1    12/2000

(Continued)

OTHER PUBLICATIONS

International Search Report dated Mar. 25, 2009.
Advisory Action dated Aug. 8, 2013 (4 pages), U.S. Appl. No. 12/677,791, filed Mar. 11, 2010.
Foreign communication from a related counterpart application—International Search Report and Written Opinion, PCT/IN2008/000586, Aug. 24, 2009, 6 pages.
Foreign communication from a related counterpart application—International Preliminary Report on Patentability, PCT/IN2008/000586, Mar. 16, 2010, 5 pages.
Foreign communication from a related counterpart application—International Search Report and Written Opinion, PCT/IB2009/053736, Feb. 9, 2010, 11 pages.

(Continued)

*Primary Examiner* — Renee E Robinson
(74) *Attorney, Agent, or Firm* — Conley Rose, P.C.; Rodney B. Carroll

(57) ABSTRACT

The present invention relates to the field of processing hydrocarbons which causes corrosion in the metal surfaces of processing units. The invention addresses the technical problem of high temperature naphthenic acid corrosion and sulphur corrosion and provides a solution to inhibit these types of corrosion. The composition formed by reacting high reactive polyisobutylene (HRPIB) with phosphorous pentasulphide in presence of catalytic amount of sulphur provides high corrosion inhibition efficiency in case of high temperature naphthenic acid corrosion inhibition and sulphur corrosion inhibition. The invention is useful in all hydrocarbon processing units, such as, refineries, distillation columns and other petrochemical industries.

35 Claims, No Drawings

(56) References Cited

U.S. PATENT DOCUMENTS

| | | |
|---|---|---|
| 7,122,508 B2 | 10/2006 | Boffa |
| 2002/0107150 A1 | 8/2002 | Mikami et al. |
| 2003/0201207 A1* | 10/2003 | Eaton et al. .................. 208/265 |
| 2005/0044778 A1 | 3/2005 | Orr |
| 2005/0234184 A1 | 10/2005 | Doring et al. |
| 2007/0119747 A1 | 5/2007 | Harrell et al. |
| 2010/0116718 A1 | 5/2010 | Subramaniyam |
| 2010/0264064 A1 | 10/2010 | Mahesh |
| 2011/0160405 A1 | 6/2011 | Subramaniyam |
| 2011/0214980 A1 | 9/2011 | Subramaniyam |

FOREIGN PATENT DOCUMENTS

| | | |
|---|---|---|
| GB | 8667 | 0/1907 |
| GB | 792553 | 3/1958 |
| WO | 2006049980 A2 | 5/2006 |
| WO | 2008005058 A1 | 1/2008 |
| WO | 2008120236 A2 | 10/2008 |
| WO | 2008120236 A3 | 10/2008 |
| WO | 2008122989 A2 | 10/2008 |
| WO | 2008122989 A3 | 10/2008 |
| WO | 2008122989 A4 | 10/2008 |
| WO | 2009063496 A2 | 5/2009 |
| WO | 2009063496 A3 | 5/2009 |
| WO | 2010023621 A2 | 3/2010 |
| WO | 2010023621 A3 | 3/2010 |
| WO | 2010023628 A1 | 3/2010 |

OTHER PUBLICATIONS

Foreign communication from a related counterpart application—International Preliminary Report on Patentability, PCT/IB2009/053736, Oct. 18, 2010, 20 pages.

Foreign communication from a related counterpart application—International Search Report and Written Opinion, PCT/IB2009/053726, Jun. 17, 2010, 15 pages.

Foreign communication from a related counterpart application—International Preliminary Report on Patentability, PCT/IB2009/053726, Dec. 7, 2010, 14 pages.

Foreign communication from a related counterpart application—International Search Report and Written Opinion, PCT/IN2008/000217, Mar. 23, 2009, 8 pages.

Foreign communication from a related counterpart application—International Preliminary Report on Patentability, PCT/IN2008/000217, Oct. 6, 2009, 7 pages.

Foreign communication from a related counterpart application—International Search Report and Written Opinion, PCT/IN2008/000195, Mar. 25, 2009, 7 pages.

Foreign communication from a related counterpart application—International Preliminary Report on Patentability, PCT/IN2008/000195, Oct. 6, 2009, 6 pages.

Office Action (Final) dated Sep. 5, 2013 (13 pages), U.S. Appl. No. 13/061,045, filed Feb. 25, 2011.

Office Action dated Jan. 29, 2013 (40 pages), U.S. Appl. No. 13/061,045, filed Feb. 25, 2011.

Office Action (Restriction Requirement) dated Dec. 7, 2012 (7 pages), U.S. Appl. No. 13/061,045, filed Feb. 25, 2011.

Office Action (Final) dated May 13, 2013 (12 pages), U.S. Appl. No. 12/594,320, filed Oct. 1, 2009.

Office Action dated Aug. 13, 2012 (15 pages), U.S. Appl. No. 12/594,320, filed Oct. 1, 2009.

Office Action (Restriction Requirement) dated Mar. 8, 2012 (9 pages), U.S. Appl. No. 12/594,320, filed Oct. 1, 2009.

Office Action (Final) dated May 23, 2013 (12 pages), U.S. Appl. No. 12/677,791, filed Mar. 11, 2010.

Office Action dated Nov. 15, 2012 (14 pages), U.S. Appl. No. 12/677,791, filed Mar. 11, 2010.

Office Action (Restriction Requirement) dated Jul. 26, 2012 (6 pages), U.S. Appl. No. 12/677,791, filed Mar. 11, 2010.

Abou El Naga, H. H., et al., "Succinimide Phosphoric Acid Esters as Multipurpose Additives," XP002565966, Lubrication Science, Jul. 1994, pp. 351-361, vol. 6, No. 4.

Office Action dated Apr. 3, 2014 (20 pages), U.S. Appl. No. 13/061,045, filed Feb. 25, 2011.

Foreign communication from a related counterpart application—Intention to Grant, European Patent Application No. 09787015.8, Mar. 27, 2014, 48 pages.

* cited by examiner

HIGH TEMPERATURE NAPHTHENIC ACID CORROSION INHIBITION USING ORGANOPHOSPHOROUS SULPHUR COMPOUNDS AND COMBINATIONS THEREOF

CROSS-REFERENCE TO RELATED APPLICATIONS

This Application is a U.S. national phase application filed under 35 U.S.C. §371 of International Application No. PCT/IN2008/000195, filed Mar. 27, 2008, designating the United States, which claims priority from Indian Patent Application No.: 604/MUM/2007, filed Mar. 30, 2007, which are hereby incorporated herein by reference in their entirety for all purposes.

FIELD OF THE INVENTION

The present invention relates to the inhibition of metal corrosion in acidic hot hydrocarbons and more particularly to the inhibition of corrosion of iron-containing metals in hot acidic hydrocarbons, especially when the acidity is derived from the presence of naphthenic acid. The invention is also useful for inhibition of sulphur corrosion.

DISCUSSION OF PRIOR ART

It is widely known in the art that the processing of crude oil and its various fractions has led to damage to piping and other associated equipment due to naphthenic acid corrosion. These are corrosive to the equipment used to distill, extract, transport and process the crudes. Generally speaking, naphthenic acid corrosion occurs when the crude being processed has a neutralization number or total acid number (TAN), expressed as the milligrams of potassium hydroxide required to neutralize the acids in a one gram sample, above 0.2. It is also known that naphthenic acid-containing hydrocarbon is at a temperature between about 200.degree. C. and 400.degree. C. (approximately 400.degree. F.-750.degree. F.), and also when fluid velocities are high or liquid impinges on process surfaces e.g. in transfer lines, return bends and restricted flow areas.

Corrosion problems in petroleum refining operations associated with naphthenic acid constituents and sulfur compounds in crude oils have been recognized for many years. Such corrosion is particularly severe in atmospheric and vacuum distillation units at temperatures between 400.degree. F. and 790.degree. F. Other factors that contribute to the corrosivity of crudes containing naphthenic acids include the amount of naphthenic acid present, the concentration of sulfur compounds, the velocity and turbulence of the flow stream in the units, and the location in the unit (e.g., liquid/vapor interface).

As commonly used, naphthenic acid is a collective term for certain organic acids present in various crude oils. Although there may be present minor amounts of other organic acids, it is understood that the majority of the acids in naphthenic based crude are naphthenic in character, i.e., with a saturated ring structure as follows:

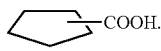

The molecular weight of naphthenic acid can extend over a large range. However, the majority of the naphthenic acid from crude oils is found in gas oil and light lubricating oil. When hydrocarbons containing such naphthenic acid contact iron-containing metals, especially at elevated temperatures, severe corrosion problems arise.

Naphthenic acid corrosion has plagued the refining industry for many years. This corroding material consists of predominantly monocyclic or bicyclic carboxylic acids with a boiling range between 350.degree. and 650.degree. F. These acids tend to concentrate in the heavier fractions during crude distillation. Thus, locations such as the furnace tubing, transfer lines, fractionating tower internals, feed and reflux sections of columns, heat exchangers, tray bottoms and condensers are primary sites of attack for naphthenic acid. Additionally, when crude stocks high in naphthenic acids are processed, severe corrosion can occur in the carbon steel or ferritic steel furnace tubes and tower bottoms. Recently interest has grown in the control of this type of corrosion in hydrocarbon processing units due to the presence of naphthenic acid in crudes from locations such as China, India, Africa and Europe.

Crude oils are hydrocarbon mixtures which have a range of molecular structures and consequent range of physical properties. The physical properties of naphthenic acids which may be contained in the hydrocarbon mixtures also vary with the changes in molecular weight, as well as the source of oil containing the acid. Therefore, characterization and behavior of these acids are not well understood. A well known method used to "quantify" the acid concentration in crude oil has been a KOH titration of the oil. The oil is titrated with KOH, a strong base, to an end point which assures that all acids in the sample have been neutralized. The unit of this titration is mg. of KOH/gram of sample and is referred to as the "Total Acid Number" (TAN) or Neutralization Number. Both terms are used interchangeably in the application.

The unit of TAN is commonly used since it is not possible to calculate the acidity of the oil in terms of moles of acid, or any other of the usual analytical terms for acid content. Refiners have used TAN as a general guideline for predicting naphthenic acid corrosion. For example, many refineries blend their crude to a TAN=0.5 assuming that at these concentrations naphthenic acid corrosion will not occur. However, this measure has been unsuccessful in preventing corrosion by naphthenic acid.

Naphthenic acid corrosion is very temperature dependent. The generally accepted temperature range for this corrosion is between 205° C. and 400° C. (400° F. and 750° F.). Corrosion attack by these acids below 205° C. has not yet been reported in the published literature. As to the upper boundary, data suggests that corrosion rates reach a maximum at about 600°-700° F. and then begin to diminish.

The concentration and velocity of the acid/oil mixture are also important factors which influence naphthenic acid corrosion. This is evidenced by the appearance of the surfaces affected by naphthenic acid corrosion. The manner of corrosion can be deduced from the patterns and color variations in the corroded surfaces. Under some conditions, the metal surface is uniformly thinned. Thinned areas also occur when condensed acid runs down the wall of a vessel. Alternatively, in the presence of naphthenic acid pitting occurs, often in piping or at welds. Usually the metal outside the pit is covered with a heavy, black sulfide film, while the surface of the pit is bright metal or has only a thin, grey to black film covering it. Moreover, another pattern of corrosion is erosion-corrosion, which has a characteristic pattern of gouges with sharp edges. The surface appears clean, with no visible by-products. The pattern of metal corrosion is indicative of the fluid flow within the system, since increased contact with surfaces allows for a greater amount of corrosion to take place. Therefore, corrosion patterns provide information as to the method of corrosion which has taken place. Also, the more complex the corrosion, i.e., in increasing complexity from uniform to pitting to erosion-corrosion, the lower is the TAN value which triggers the behavior.

The information provided by corrosion patterns indicates whether naphthenic acid is the corroding agent, or rather if the process of corrosion occurs as a result of attack by sulfur. Most crude contain hydrogen sulfide, and therefore readily form iron sulfide films on carbon steel. In all cases that have been observed in the laboratory or in the field, metal surfaces have been covered with a film of some sort. In the presence of hydrogen sulfide the film formed is invariably iron sulfide, while in the few cases where tests have been run in sulfur free conditions, the metal is covered with iron oxide, as there is always enough water or oxygen present to produce a thin film on the metal coupons.

Tests utilized to determine the extent of corrosion may also serve as indicators of the type of corrosion occurring within a particular hydrocarbon treating unit. Metal coupons can be inserted into the system. As they are corroded, they lose material. This weight loss is recorded in units of $mg/cm^2$. Thereafter, the corrosion rate can be determined from weight loss measurements. Then the ratio of corrosion rate to corrosion product ($mpy/mg/cm^2$) is calculated. This is a further indicator of the type of corrosion process which has taken place, for if this ratio is less than 10, it has been found that there is little or no contribution of naphthenic acid to the corrosion process. However, if the ratio exceeds 10, then naphthenic acid is a significant contributor to the corrosion process.

Distinguishing between sulfidation attack and corrosion caused by naphthenic acid is important, since different remedies are required depending upon the corroding agent. Usually, retardation of corrosion caused by sulfur compounds at elevated temperatures is effected by increasing the amount of chromium in the alloy which is used in the hydrocarbon treating unit. A range of alloys may be employed, from 1.25% Cr to 12% Cr, or perhaps even higher. Unfortunately, these show little to no resistance to naphthenic acid. To compensate for the corroding effects of sulfur and naphthenic acid, an austenitic stainless steel which contains at least 2.5% molybdenum, must be utilized. The corrosive problem is known to be aggravated by the elevated temperatures necessary to refine and crack the oil and by the oil's acidity which is caused primarily by high levels of naphthenic acid indigenous to the crudes. Naphthenic acids is corrosive between the range of about 175° C. to 420° C. At the higher temperatures the naphthenic acids are in the vapor phase and at the lower temperatures the corrosion rate is not serious. The corrosivity of naphthenic acids appears to be exceptionally serious in the presence of sulfide compounds, such as hydrogen sulfide, mercaptans, elemental sulfur, sulfides, disulfides, polysulfides and thiophenols. Corrosion due to sulfur compounds becomes significant at temperatures as low as 450° F. The catalytic generation of hydrogen sulfide by thermal decomposition of mercaptans has been identified as a cause of sulfidic corrosion.

Sulfur in the crudes, which produces hydrogen sulfide at higher temperatures, also aggravates the problem. The temperature range of primary interest for this type of corrosion is in the range of about 175° C. to about 400° C., especially about 205° C. to about 400° C.

Various approaches to controlling naphthenic acid corrosion have included neutralization and/or removal of naphthenic acids from the crude being processed; blending low acid number oils with corrosive high acid number oils to reduce the overall neutralization number; and the use of relatively expensive corrosion-resistant alloys in the construction of the piping and associated equipment. These attempts are generally disadvantageous in that they require additional processing and/or add substantial costs to treatment of the crude oil. Alternatively, various amine and amide based corrosion inhibitors are commercially available, but these are generally ineffective in the high temperature environment of naphthenic acid corrosion. Naphthenic acid corrosion is readily distinguished from conventional fouling problems such as coking and polymer deposition which can occur in ethylene cracking and other hydrocarbon processing reactions using petroleum based feedstocks. Naphthenic acid corrosion produces a characteristic grooving of the metal in contact with the corrosive stream. In contrast; coke deposits generally have corrosive effects due to carburization, erosion and metal dusting.

Because these approaches have not been entirely satisfactory, the accepted approach in the industry is to construct the distillation unit, or the portions exposed to naphthenic acid/sulfur corrosion, with the resistant metals such as high quality stainless steel or alloys containing higher amounts of chromium and molybdenum. The installation of corrosion-resistant alloys is capital intensive, as alloys such as 304 and 316 stainless steels are several times the cost of carbon steel. However, in units not so constructed there is a need to provide inhibition treatment against this type of corrosion. The prior art corrosion inhibitors for naphthenic acid environments include nitrogen-based filming corrosion inhibitors. However, these corrosion inhibitors are relatively ineffective in the high temperature environment of naphthenic acid oils.

While various corrosion inhibitors are known in various arts, the efficacy and usefulness of any particular corrosion inhibitor is dependent on the particular circumstances in which it is applied. Thus, efficacy or usefulness under one set of circumstances often does not imply the same for another set of circumstances. As a result, a large number of corrosion inhibitors have been developed and are in use for application to various systems depending on the medium treated, the type of surface that is susceptible to the corrosion, the type of corrosion encountered, and the conditions to which the medium is exposed. For example, U.S. Pat. No. 3,909,447 describes certain corrosion inhibitors as useful against corrosion in relatively low temperature oxygenated aqueous systems such as water floods, cooling towers, drilling muds, air drilling and auto radiator systems. That patent also notes that many corrosion inhibitors capable of performing in non-aqueous systems and/or non-oxygenated systems perform poorly in aqueous and/or oxygenated systems. The reverse is true as well. The mere fact that an inhibitor that has shown efficacy in oxygenated aqueous systems does not suggest that it would show efficacy in a hydrocarbon. Moreover, the mere fact that an inhibitor has been efficacious at relatively low temperatures does not indicate that it would be efficacious at elevated temperatures. In fact, it is common for inhibitors that are very effective at relatively low temperatures to become ineffective at temperatures such as the 175° C. to 400° C. encountered in oil refining. At such temperatures, corrosion is notoriously troublesome and difficult to alleviate. Thus, U.S. Pat. No. 3,909,447 contains no teaching or suggestion that it would be effective in non-aqueous systems such as hydrocarbon fluids, especially hot hydrocarbon fluids. Nor is there any indication in U.S. Pat. No. 3,909,447 that the compounds disclosed therein would be effective against naphthenic acid corrosion under such conditions.

Atmospheric and vacuum distillation systems are subject to naphthenic acid corrosion when processing certain crude oils. Currently used treatments are thermally reactive at use temperatures. In the case of phosphorus-based inhibitors, this is thought to lead to a metal phosphate surface film. The film is more resistant to naphthenic acid corrosion than the base steel. These inhibitors are relatively volatile and exhibit fairly narrow distillation ranges. They are fed into a column above or below the point of corrosion depending on the temperature range. Polysulfide inhibitors decompose into complex mixtures of higher and lower polysulfides and, perhaps, elemental sulfur and mercaptans. Thus, the volatility and protection offered is not predictable.

The problems caused by naphthenic acid corrosion in refineries and the prior art solutions to that problem have been described at length in the literature, the following of which are representative:

U.S. Pat. No. 3,531,394 to Koszman described the use of phosphorus and/or bismuth compounds in the cracking zone of petroleum steam furnaces to inhibit coke formation on the furnace tube walls.

U.S. Pat. No. 4,024,049 to Shell et al discloses compounds substantially as described and claimed herein for use as refinery antifoulants. While effective as antifoulant materials, materials of this type have not heretofore been used as corrosion inhibitors in the manner set forth herein. While this reference teaches the addition of thiophosphate esters such as those used in the subject invention to the incoming feed, due to the non-volatile nature of the ester materials they do not distill into the column to protect the column, the pumparound piping, or further process steps. I have found that by injecting the thiophosphate esters as taught herein, surprising activity is obtained in preventing the occurrence of naphthenic acid corrosion in distillation columns, pumparound piping, and associated equipment.

U.S. Pat. No. 4,105,540 to Weinland describes phosphorus containing compounds as antifoulant additives in ethylene cracking furnaces. The phosphorus compounds employed are mono- and di-ester phosphate and phosphite compounds having at least one hydrogen moiety complexed with an amine.

U.S. Pat. No. 4,443,609 discloses certain tetrahydrothiazole phosphonic acids and esters as being useful as acid corrosion inhibitors. Such inhibitors can be prepared by reacting certain 2,5-dihydrothiazoles with a dialkyl phosphite. While these tetrahydrothiazole phosphonic acids or esters have good corrosion and inhibition properties, they tend to break down during high temperature applications thereof with possible emission of obnoxious and toxic substances.

It is also known that phosphorus-containing compounds impair the function of various catalysts used to treat crude oil, e.g., in fixed-bed hydrotreaters and hydrocracking units. Crude oil processors are often in a quandary since if the phosphite stabilizer is not used, then iron can accumulate in the hydrocarbon up to 10 to 20 ppm and impair the catalyst. Although nonphosphorus-containing inhibitors are commercially available, they are generally less effective than the phosphorus-containing compounds.

U.S. Pat. No. 4,542,253 to Kaplan et al, described an improved method of reducing fouling and corrosion in ethylene cracking furnaces using petroleum feedstocks including at least 10 ppm of a water soluble mine complexed phosphate, phosphite, thiophosphate or thiophosphite ester compound, wherein the amine has a partition coefficient greater than 1.0 (equal solubility in both aqueous and hydrocarbon solvents).

U.S. Pat. No. 4,842,716 to Kaplan et al describes an improved method for reducing fouling and corrosion at least 10 ppm of a combination of a phosphorus antifoulant compound and a filming inhibitor. The phosphorus compound is a phosphate, phosphite, thiophosphate or thiophosphite ester compound. The filming inhibitor is an imidazoline compound.

U.S. Pat. No. 4,941,994 Zetmeisl et al discloses a naphthenic acid corrosion inhibitor comprising a dialkyl or trialkylphosphite in combination with an optional thiazoline.

A significant advancement in phosphorus-containing naphthenic acid corrosion inhibitors was reported in U.S. Pat. No. 4,941,994. Therein it is disclosed that metal corrosion in hot acidic liquid hydrocarbons is inhibited by the presence of a corrosion inhibiting amount of a dialkyl and/or trialkyl phosphite with an optional thiazoline.

While the method described in U.S. Pat. No. 4,941,994 provides significant improvements over the prior art techniques, nevertheless, there is always a desire to enhance the ability of corrosion inhibitors while reducing the amount of phosphorus-containing compounds which may impair the function of various catalysts used to treat crude oil, as well as a desire for such inhibitors that may be produced from lower cost or more available starting materials.

Another approach to the prevention of naphthenic acid corrosion is the use of a chemical agent to form a barrier between the crude and the equipment of the hydrocarbon processing unit. This barrier or film prevents corrosive agents from reaching the metal surface, and is generally a hydrophobic material. Gustavsen et al. NACE Corrosion 89 meeting, paper no. 449, Apr. 17-21, 1989 details the requirements for a good filming agent. U.S. Pat. No. 5,252,254 discloses one such film forming agent, sulfonated alkyl-substituted phenol, and effective against naphthenic acid corrosion.

U.S. Pat. No. 5,182,013 issued to Petersen et al. on Jan. 26, 1993 describes another method of inhibiting naphthenic acid corrosion of crude oil, comprising introducing into the oil an effective amount of an organic polysulfide. The disclosure of U.S. Pat. No. 5,182,013 is incorporated herein by reference. This is another example of a corrosion-inhibiting sulfur species. Sulfidation as a source of corrosion was detailed above. Though the process is not well understood, it has been determined that while sulfur can be an effective anti-corrosive agent in small quantities, at sufficiently high concentrations, it becomes a corrosion agent.

Phosphorus can form an effective barrier against corrosion without sulfur, but the addition of sulfiding agents to the process stream containing phosphorus yields a film composed of both sulfides and phosphates. This results in improved performance as well as a decreased phosphorus requirement. This invention pertains to the deliberate addition of sulfiding agents to the process stream when phosphorus-based materials are used for corrosion control to accentuate this interaction.

Organic polysulfides (Babaian-Kibala, U.S. Pat. No. 5,552,085), organic phosphites (Zetlmeisl, U.S. Pat. No. 4,941,994), and phosphate/phosphite esters (Babaian-Kibala, U.S. Pat. No. 5,630,964), have been claimed to be effective in hydrocarbon-rich phase against naphthenic acid corrosion. However, their high oil solubility incurs the risk of distillate side stream contamination by phosphorus.

Phosphoric acid has been used primarily in aqueous phase for the formation of a phosphate/iron complex film on steel surfaces for corrosion inhibition or other applications (Coslett, British patent 8,667, U.S. Pat. Nos. 3,132,975, 3,460,989 and 1,872,091). Phosphoric acid use in high temperature non-aqueous environments (petroleum) has also been reported for purposes of fouling mitigation (U.S. Pat. No. 3,145,886).

There remains a continuing need to develop additional options for mitigating the corrosivity of acidic crudes at lower cost. This is especially true at times of low refining margins and a high availability of corrosive crudes from sources such as Europe, China, or Africa, and India. The present invention addresses this need.

In view of above, there is a need to provide a composition to provide effective high temperature naphthenic acid corrosion inhibition as well as sulphur corrosion inhibition, which will overcome the disadvantages of the prior-art compositions.

OBJECTS AND ADVANTAGES OF PRESENT INVENTION

Accordingly, the objects and advantages of the present invention are described below.

An object of present invention is to provide a chemical composition which will provide very effective high temperature naphthenic acid corrosion inhibition as well as sulphur corrosion inhibition.

Another object of the present invention is to provide a corrosion inhibiting composition, which is very stable even at high temperature.

Yet another object of the present invention is to provide a corrosion inhibiting composition, having very low acid value.

SUMMARY OF INVENTION

The present invention relates to the field of processing hydrocarbons which causes corrosion in the metal surfaces of processing units. The invention addresses the technical problem of high temperature naphthenic acid corrosion and sulphur corrosion and provides a solution to inhibit these types of corrosion. The composition formed by reacting high reactive polyisobutylene (HRPIB) with phosphorous pentasulphide in presence of catalytic amount of sulphur provides high corrosion inhibition efficiency in case of high temperature naphthenic acid corrosion inhibition and sulphur corrosion inhibition. The invention is useful in all hydrocarbon processing units, such as, refineries, distillation columns and other petrochemical industries.

DESCRIPTION OF THE INVENTION

The present invention uses the following reacted compound to be used as corrosion inhibitor for inhibiting high temperature nephthenic acid corrosion. This reacted compound is obtained by reaction of hydrocarbon $R_1$ such as olefins with $P_2S_5$ (Phosphorus pentasulphide) in presence of sulphur powder. The preferred olefins have double bonds, wherein double bond is present internally or terminally. The details about said hydrocarbon $R_1$ are given below.

As previously mentioned, the term "hydrocarbon" as used herein means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

Preferably $R_1$ is an optionally substituted alkyl or alkenyl group. In one aspect $R_1$ is an optionally substituted alkyl group. In another aspect, $R_1$ is an optionally substituted alkenyl group.

The term "alkenyl" refers to a branched or straight chain hydrocarbon, which can comprise one or more carbon-carbon double bonds. Exemplary alkenyl groups include propylenyl, butenyl, isobutenyl, pentenyl, 2,2-methylbutenyl, 3-methylbutenyl, hexanyl, heptenyl, octenyl, and polymers thereof.

In one aspect $R_1$ is an optionally substituted branched alkyl or alkenyl group. Preferably, $R_1$ is a polyisobutenyl (PIB) group.

Conventional PIBs and so-called "high-reactivity" PIBs (see for example EP-B-0565285) are suitable for use in this invention. High reactivity in this context is defined as a PIB wherein at least 50%, preferably 70% or more, of the terminal olefinic double bonds are of the vinylidene type, for example the GLISSOPAL compounds available from BASF.

In one aspect $R_1$ has between 10 and 1000 carbon atoms, preferably between 4 and 200 carbon atoms.

In one aspect, $R_1$ has a molecular weight of from 200 to 10000, preferably from 200 to 1300.

The example of internally double bonded olefins include beta-olefins.

The ratio of $P_2S_5$ to Olefin is preferably 0.05 to 2 mole of $P_2S_5$ to 1 mole of Olefins. The Sulphur powder is present in catalytic quantity, that is, sulphur powder is 0.5% to 5% of Olefin by weight.

The most preferred embodiment of the present invention is described below:

A weighed quantity of HRPIB (High Reactive Polyisobutylene), phosphorous pentasulphide and sulphur powder are charged into a clean four-necked round bottom flask, equipped with nitrogen inlet, stirrer and thermometer, thereby forming a reaction mixture.

This reaction mixture is stirred and heated to temperature of 160° C. under nitrogen gas purging. At this temperature of 160° C., the reaction leads to evolution of hydrogen sulphide gas ($H_2S$). The temperature of the reaction mixture is now maintained between 160° C. to 180° C., for a period of 1 hour to 2 hours. Then the temperature of the mixture is raised to 220° C. The reaction mixture is then maintained at this temperature of 220° C. for 6 hours.

The resultant reaction mass is then cooled to temperature of 100° C., when nitrogen gas is purged into the resultant reaction mass, to drive out the hydrogen sulphide present therein. The resulting polyisobutylene phosphorous sulphur compound is used as a high temperature naphthenic acid corrosion inhibitor. This compound is used neat or diluted in appropriate solvent such as xylene, toluene, and aromatic solvent as any other appropriate solvent to achieve inhibition of high temperature naphthenic acid corrosion.

The present invention is directed to a method for inhibiting corrosion on the metal surfaces of the processing units which process hydrocarbons such as crude oil and its fractions containing naphthenic acid. The invention is explained in details in its simplest form wherein the following method steps are carried out, when it is used to process crude oil in process units such as distillation unit. Similar steps can be used in different processing units such as, pumparound piping, heat exchangers and such other processing units.

These method steps are explained below:
 a) heating the hydrocarbon containing naphthenic acid to vaporize a portion of the hydrocarbon:
 b) allowing the hydrocarbon vapors to rise in a distillation column;
 c) condensing a portion of the hydrocarbon vapours passing through the distillation column to produce a distillate;

d) adding to the distillate, from 5 to 2000 ppm of a polyisobutylene phosphorous sulphur compound of instant invention;

e) allowing the distillate containing polyisobutylene phosphorous sulphur compound to contact substantially the entire metal surfaces of the distillation unit to form protective film on such surface, whereby such surface is inhibited against corrosion.

It is advantageous to treat distillation column, trays, pumparound piping and related equipment to prevent naphthenic acid corrosion, when condensed vapours from distilled hydrocarbon fluids contact metallic, equipment at temperatures greater than 200° C., and preferably 400° C. The polyisobutylene phosphorous sulphur compound additive is generally added to the condensed distillate and the condensed distillate is allowed to contact the metallic surfaces of the distillation column, packing, trays, pump around piping and related equipment as the condensed distillate passes down the column and into the distillation vessel. The distillate may also be collected as product. The corrosion inhibitors of the instant invention remain in the resultant collected product.

In commercial practice, the additives of this invention may be added to a distillate return to control corrosion in a draw tray and in the column packing while a second injection may be added to a spray oil return immediately below the draw trays to protect the tower packing and trays below the distillate draw tray. It is not so critical where the additive of the invention is added as long as it is added to distillate that is later returned to the distillation vessel, or which contact the metal interior surfaces of the distillation column, trays, pump around piping and related equipments.

The method of using the polyisobutylene phosphorous sulphur compound of the present invention for achieving inhibition of high temperature naphthenic acid corrosion is explained below with the help of examples 1 to 4.

The detailed discussion given below with respect to the results presented in Table I to V for experiments described in Examples 1 to 4 explains the effectiveness of the additive compound of present invention in high temperature, naphthenic acid corrosion inhibition or sulphur corrosion inhibition.

Referring to Table 1 where molar ratio of HRPIB to phosphorous pentasulphide was 1:1, it is observed that, in the static test, as the effective dosage of additive compound of the present invention was increased from 150 ppm to 325 ppm, the corrosion inhibition efficiency, as calculated by formula given in Example 2, increased from 55.75% to 99.67%.

Referring to Table II, where molar ratio of HRPIB to phosphorous pentasulphide was 1:0.25, it is observed that, as the effective dosage of additive compound of the present invention was increased from 250 ppm to 750 ppm, the corrosion inhibition efficiency, as calculated by formula given in Example 2, increased from 42.3% to 97.72%.

Referring to Table III, where normal polyisobutylene was used and molar ration of normal polyisobutylene to phosphorous pentasulphide was 1:0.35, the corrosion inhibition efficiency, as calculated by formula given in Example 2, was 54.39% when effective dosage of 300 ppm of additive compound of present invention was used.

Referring to the Table IV, it was observed that, in the dynamic test with passivated coupons, with molar ratio of Polyisobutylene to phosphorous pentasulphide being 1:1 and with effective dosage of additive compound of present invention maintained at 5 ppm, the corrosion inhibition efficiency increased from 81.16% to 85.48% as the passivation dose increased from 250 ppm to 500 ppm.

Again referring to Table IV, in the dynamic test as the effective dosage of additive compound, of present invention, increased from 5 ppm to 15 ppm, (keeping the passivation dosage same, that is, 500 ppm) the corrosion inhibition efficiency, as calculated by given formula given in Example 2, increased from 85.48% to 100%.

Referring to Table V, it is observed that the additive compound of the present invention is also effective in controlling high temperature corrosion of metal surfaces in contact with hydrocarbon streams with high sulphur content.

Thus it is seen from the earlier discussion that the additive compound of present invention used for corrosion-inhibition has the following important distinguishing features, as compared to the prior art.

1) The inventor of the present invention, after extensive experimentation, has surprisingly found that the additive compound used by the inventor, that is, additive compound formed by reacting High Reactive Polyisobutylene or Normal Polyisobutylene, with Phosphorous Pentasulphide, in the only POLYMERIC ADDITIVE, which is highly effective in high temperature corrosion inhibition, as shown by the experimental results given in Tables I and V.

The prior-art does not teach or suggest use of a polymeric additive in naphthenic acid corrosion inhibition or sulphur corrosion inhibition or any corrosion inhibition, in general.

2) Another distinguishing feature of the additive compound of present invention is that it has more thermal stability as compared to the additive compounds taught by the prior-art, due to the polymeric nature of the additive compound of present invention. Due to its high thermal stability the additive compound of present invention is very effective in high temperature naphthenic corrosion inhibition or high temperature sulphur corrosion.

3) Yet another distinguishing feature of the additive compound of present invention is that, it has very low acidity as compared to the additive compounds of prior art, for example, the phosphate esters of prior art has very high acidity. The phosphate esters of prior art are known to have a tendency to decompose, even at lower temperatures, to form phosphoric acids, which travel further along the hydrocarbon stream and react with metal surfaces of equipments such as packing of distillation column, to form solid iron phosphate. These solids plug the holes of equipments and thereby lead to fouling of distillation column.

The additive compound of the present invention does not have this deficiency.

EXAMPLE 1

The weighed quantities of 68.16 gm of commercially available HRPIB (High Reactive Polyisobutylene with molecular weight 950 approximately), 30.31 gm of Phosphorous Pentasulphide and 1.51 gm of Sulphur Powder are charged into a clean four necked round bottom flask, equipped with $N_2$ inlet, stirrer and thermometer, thereby forming a reaction mixture. This gives 1:1 mole ratio of Phosphorous Pentasulphide to Olefin.

The reaction mixture was stirred and heated to 160° C. temperature under nitrogen gas purging. The purging of $N_2$ gas led to removal of hydrogen sulphide gas, which was generated during the reaction. The temperature of the reaction mixture was maintained between 160° C. to 180° C., for a period of 1 hour to 2 hours. Then the temperature of the mixture was raised to 220° C. and the mixture was maintained at this temperature for 6 to 10 hours.

The resultant reaction mass was then cooled to 100° C. when nitrogen gas was purged into it, to drive out the hydrogen sulphide gas present therein. The resulting polyisobutylene phosphorous sulphur compound was used as a high temperature naphthenic acid corrosion inhibitor, as well as, sulphur corrosion inhibitor. This compound was used neat or diluted in appropriate solvent such as xylene, toluene, and aromatic solvent as well as any other appropriate solvent to achieve inhibition of high temperature naphthenic acid corrosion as well as sulphur corrosion.

The above mentioned synthesis is carried out for different mole ratios of HRPIB to Phosphorous Pentasulphide. A similar synthesis was carried out by using normal polyisobutylene instead of HRPIB.

EXAMPLE 2

High Temperature Naphthenic Acid Corrosion Test

In this example, various amounts of a 50% formulation of the composition prepared in accordance, with Example 1, were tested for corrosion inhibition efficiency on steel coupons in hot oil containing naphthenic acid. A weight loss coupon, immersion test was used to evaluate the invention compound for its effectiveness in inhibition of naphthenic acid corrosion at 290° C. temperature. Different dosage such as 300, 400 and 600 ppm of invention compound were used, as 50% active solution.

A static test on steel coupon was conducted without using any additive. This test provided a blank test reading.

The reaction apparatus consisted of a one-liter four necked round bottom flask equipped with water condenser, $N_2$ purger tube, thermometer pocket with thermometer and stirrer rod. 600 gm (about 750 ml) paraffin hydrocarbon oil (D-130) was taken in the flask. $N_2$ gas purging was started with flow rate of 100 cc/minute and the temperature was raised to 100° C., which temperature was maintained for 30 minutes. A compound of example 1 comprising Polyisobutylene and Phosphorous Pentasulphide with sulphur powder was added to the reaction mixture. The reaction mixture was stirred for 15 minutes at 100° C. temperature. After removing the stirrer, the temperature of the reaction mixture was raised to 290° C. A pre-weighed weight-loss carbon steel coupon CS 1010 with dimensions 76 mm . . . times 13 mm . . . times 1.6 mm was immersed. After maintaining this condition for 1 hour to 1.5 hours, 31 gm of naphthenic acid (commercial grade with acid value of 230 mg/KOH) was added to the reaction mixture. A sample of one gm weight of reaction mixture was collected for determination of acid value, which was found to be approximately 11.7. This condition was maintained for four hours. After this procedure, the metal coupon was removed, excess oil was rinsed away, the excess corrosion product was removed from the metal surface. Then the metal coupon was weighed and the corrosion rate was calculated in mils per year.

Calculation of Corrosion Inhibition Efficiency.

The method used in calculating Corrosion Inhibition Efficiency is given below. In this calculation, corrosion inhibition efficiency provided by additive compound is calculated by comparing weight loss due to additive with weight loss of blank coupon (without any additive).

$$\text{Corrosion Inhibition Efficiency} = \frac{(\text{Weight loss for blank without additive}) - (\text{weight loss with additive})}{(\text{weight loss for blank without additive})} \times 100$$

The calculated magnitudes are entered in the Tables in appropriate columns.

The results of the experiments are presented in Table I and II.

The test results of the experiments conducted by using normal polyisobutylene are given in Table III.

The corrosion rate in MPY (mils per year) is calculated by the formula, $$MPY = \frac{534 \times \text{Weight loss in mg}}{(\text{Density in gm/cc}) \times (\text{Area in in}^2) \times (\text{Time of test in hours})}$$

EXAMPLE 3

High Temperature Naphthenic Acid Corrosion Dynamic Test

The dynamic testing was carried out by using rotating means provided in the temperature-controlled autoclave and was carried out by using passivated steel coupons. A dynamic test on steel coupon was conducted without using any additive. This test provided a blank test reading. The passivation procedure is explained below:

Passivation Procedure 600 gm of paraffin hydrocarbon oil (D-130) was taken in a reaction vessel comprising a four necked round bottom flask equipped with water condenser, $N_2$ purger tube, thermometer pocket with thermometer and stirrer rod. $N_2$ gas was purged. For passivation of the steel coupon, various amounts of compound of Example 1, for example, 250, 500 and 1000 ppm, (each of which included 50% active additive compound), were added to this reaction mixture. The reaction mixture was stirred for 15 minutes at 100° C. temperature. After removing the stirrer, the temperature of the reaction mixture was raised to 290° C. A pre-weighed weight-loss coupon CS 1010 with dimensions 76 mm . . . times 13 mm . . . times 1.6 mm was immersed. After maintaining this condition for 4 hours, the steel coupon was removed, excess oil was rinsed away, and the coupon was dried. The metal coupon was weighed. This formed the pre-passivated coupon.

In this example, various amounts of a 50% formulation of the composition prepared in accordance, with Example 1, were tested dynamically for corrosion inhibition efficiency on steel coupons in a hot oil containing naphthenic acid. A weight-loss coupon immersion dynamic test was used to evaluate the invention compound for its effectiveness in inhibition of naphthenic acid corrosion at 290° C. temperature in dynamic condition.

The following test equipment and materials were used in the Dynamic Corrosion Test:
2. Temperature controlled autoclave
3. Preweighed weight-loss carbon steel coupons CS 1010 with dimensions 76 mm . . . times 13 mm . . . times 1.6 mm.
4. Means to rotate the coupon, to provide a peripheral velocity in excess of 3 m/second.

Material:
1. Paraffin hydrocarbon oil (D-130) with naphthenic acid added to provide an acid neutralization number of approximately 2 mg/KOH.
2. Nitrogen gas in the vapour space.

Two pre-weighed and pre-passivated weight-loss carbon steel coupons, were clamped to the rotating means of the autoclave. The dynamic test was conducted at 290° C. for 4 hours. After the test, the coupons were removed, excess oil was rinsed away, excess corrosion product was removed from the surface of coupons. The coupons were then weighed and the corrosion rate was calculated as mils/year. The results of this dynamic test are presented in Table IV.

EXAMPLE 4

High Temperature Sulphur Corrosion Dynamic Test

Testing procedure, similar to that used in Example 3 was adopted for evaluating corrosion inhibition efficiency in sulphur-rich stream like Vacuum Residue.

It is known to the person skilled in the art, that, in a refinery, bottom stream of the atmospheric distillation tower is further distilled under vacuum. Bottom stream of the Vacuum distillation tower is called as Vacuum Residue (VR). VR is also popularly known as Short Residue. In crude assay, VR is generally defined as stream with boiling point of 565+ deg C. This stream generally contains highest amount of metals in all streams coming out from atmospheric & vacuum distillation unit. VR is further treated to form either Fuel Oil or Petroleum Coke. VR is also defined as Heavy Hydrocarbon Mixture (of Paraffinic and Bitumastic Materials containing mainly C24+.

The elemental composition of VR used for this dynamic test indicated content of approximately 5% sulphur with TAN of 0.55 mg/KOH. This VR was obtained from refinery located in Western part of India. The results of this dynamic test are provided in Table V.

TABLE I

STATIC TEST (with molar ratio of Polyisobutylene to Phosphorous Pentasulphide = 1:1) (EXAMPLE-2)

| Experiment No. | Compound | Dosage in ppm | Effective Dosage in ppm | Weight Loss in mg | Corrosion Rate MPY | Corrosion Inhibition efficiency |
|---|---|---|---|---|---|---|
| 1 | — (Only blank) | — | — | 89.5 | 529.89 | 0 |
| 2 | Composition as per Example 1 | 300 | 150 | 39.6 | 232.24 | 55.75 |
| 3 | Composition as per Example 1 | 400 | 200 | 15.2 | 89.114 | 83.02 |
| 4 | Composition as per Example 1 | 600 | 300 | 3.8 | 12.31 | 95.75 |
| 5 | Composition as per Example 1 | 650 | 325 | 0.3 | 1.5 | 99.67 |

TABLE II

STATIC TEST (with molar ratio of Polyisobutylene to Phosphorous Pentasulphide = 1:0.25) (EXAMPLE-2)

| Experiment No. | Compound | Dosage in ppm | Effective Dosage in ppm | Weight Loss in mg | Corrosion Rate MPY | Corrosion Inhibition efficiency |
|---|---|---|---|---|---|---|
| 6 | — (Only blank) | — | — | 87.7 | 439 | 0 |
| 7 | Composition as per Example 1 | 500 | 250 | 50.6 | 253.3 | 42.3 |
| 8 | Composition as per Example 1 | 1000 | 500 | 14.2 | 71.08 | 83.81 |
| 9 | Composition as per Example 1 | 1500 | 750 | 2.0 | 10.1 | 97.72 |

TABLE III

STATIC TEST (with molar ratio of Normal Polyisobutylene to Phosphorous Pentasulphide = 1:0.35)

| Experiment No. | Compound | Dosage in ppm | Effective Dosage in ppm | Weight Loss in mg | Corrosion Rate MPY | Corrosion Inhibition efficiency |
|---|---|---|---|---|---|---|
| 6 | — (Only blank) | — | — | 87.7 | 439 | 0 |
| 10 | Composition as per Example 1 | 600 | 300 | 40 | 200.21 | 54.39 |

TABLE IV

DYNAMIC TEST WITH PASSIVATED COUPONS (with molar ration of Polyisobutylene to Phosphorous Pentasulphide 1:1)

| Experiment No. | Compound | Dosage in ppm | Effective Dosage in ppm | Weight Loss in mg | Corrosion Rate MPY | Corrosion Inhibition efficiency | Passivation Dose in ppm |
|---|---|---|---|---|---|---|---|
| 11 | — (Only blank) | — | — | 6.9 | 34.5 | 0 | — |
| 12 | Composition as per Example 1 | 10 | 5 | 1.0 | 5.01 | 85.48 | 500 |
| 13 | Composition as per Example 1 | 10 | 5 | 1.3 | 6.5 | 81.16 | 250 |
| 14 | Composition as per Example 1 | 30 | 15 | 0 | NIL | 100 | 500 |

TABLE V

HIGH TEMPERATURE CORROSION TEST RESULT (DYNAMIC) - VR SAMPLE

| Sr. No. | Doses (ppm) | Product (1st step) | Wt. loss (mg) | Corr. Rate (MPY) | Efficiency (%) |
|---|---|---|---|---|---|
| 1 | — | Blank | 8.15 | 27.19 | — |
| 2 | 20 | Composition as per Example 1 | 2.3 | 7.6 | 72.0 |

In view of the details given in foregoing description of the present invention, it will be apparent to a person skilled in the art that the present invention basically comprises the following items:

Item 1
A naphthenic-acid-corrosion-inhibiting composition comprising olefin phosphorous sulphur compound, produced by reacting said olefin with phosphorous pentasulphide in presence of catalytic amount of sulphur, capably forming a reaction mixture, wherein, the molar ratio of said olefin to said phosphorous pentasulphide, is between 1:0.05 to 1:1.5, preferably 1:1.

Item 2
A naphthenic-acid-corrosion-inhibiting composition, as described in item 1, wherein said olefin is polyisobutylene, which is high reactive or normal.

Item 3
A naphthenic-acid-corrosion-inhibiting and sulphur-corrosion-inhibiting composition, as described in item 2, wherein said composition is arrived at, by stirring and heating said reaction mixture of claim 2, to 160° C. under nitrogen gas purging, maintaining said reaction mixture between 160° C. to 180° C. for a period of 1 hour to 2 hours, raising temperature of said reaction mixture to from 185° C. to 250° C., preferably from 190° C. to 230° C., more preferably from 210° C. to 225° C. and maintaining said reaction mixture with raised temperature for 1 to 24 hours, preferably for 6 to 10 hours, cooling the reaction mass to 100° C. and purging nitrogen gas into reaction vessel to drive out the hydrogen sulphide gas, thereby resulting into said composition.

Item 4
A composition according to items 1, 2 or 3 wherein said olefin is an optionally substituted hydrocarbon group.

Item 5
A composition according to any one of the preceding items wherein said olefin is an optionally substituted alkyl or alkenyl group.

Item 6
A composition according to any one of the preceding items wherein said olefin is an optionally substituted branched alkyl or alkenyl group.

Item 7
A composition according to any one of the preceding items wherein said olefin is a polyisobutenyl group.

Item 8
A composition according to any one of the preceding items wherein said olefin has between 10 and 1000 carbon atoms.

Item 9
A composition according to any one of the preceding items wherein said olefin has between 4 and 100 carbon atoms.

Item 10
A composition according to any one of the preceding items wherein said olefin has a molecular weight of from 200 to 10,000.

Item 11
A composition according to any one of the preceding items wherein olefin has a molecular weight of approximately 250 to approximately 1300.

Item 12
A process for high temperature naphthenic acid corrosion inhibition and/or sulphur corrosion inhibition of metallic surfaces of any of the hydrocarbon, wherein processing units of a petrochemical plant, with said processing units comprising distillation columns, strippers, trays, pumparound piping and related equipments, using organophosphorous sulphur compounds, comprising the steps of:
  a) heating the hydrocarbon containing naphthenic acid and/or sulphur compounds, to vapourize a portion of said hydrocarbon;
  b) condensing a portion of the hydrocarbon vapours, passing through said hydrocarbon processing unit, to produce a condensed distillate;
  c) adding to said distillate, before said condensed distillate is returned to said hydrocarbon processing unit or collected as a product, from 1 to 2000 ppm of a olefin phosphorous sulphur compound, in corrosion-inhibition-effective-amount, capably forming a reaction mixture;
  d) allowing said condensed distillate containing said olefin phosphorous sulphur compound, to contact said metallic surfaces of said hydrocarbon processing unit, to form a protective film on said surfaces whereby each surface is inhibited against corrosion; and
  e) allowing said condensed distillate to return to said hydrocarbon processing unit, or to be collected as said product.

Item 13

A process, as described in item 12, wherein said olefin of step (c) and (d) of item 12, comprises polyisobutylene, which is high reactive or normal.

Although the invention has been described with reference to certain preferred embodiments, the invention is not meant to be limited to those preferred embodiments. Alterations to the preferred embodiments described are possible without departing from the spirit of the invention. However, the process and composition described above is intended to be illustrative only, and the novel characteristics of the invention may be incorporated in other forms without departing from the scope of the invention.

The invention claimed is:

1. A naphthenic acid corrosion inhibiting composition comprising olefin phosphorous sulphur compound, wherein the composition is produced by reacting olefin with phosphorous pentasulphide to form a reaction mixture comprising said olefin phosphorous sulphur compound, wherein the molar ratio of said olefin to said phosphorous pentasulphide is between 1:0.05 to 1:1.5, and wherein said reaction of the olefin with the phosphorous pentasulphide is carried out in multi-step heating and in presence of catalytic amount of sulphur, and under nitrogen gas purging, and thereby resulting into said composition.

2. A naphthenic acid corrosion inhibiting composition of claim 1, wherein said olefin is polyisobutylene, which is high reactive or normal.

3. A naphthenic acid corrosion inhibiting and sulphur corrosion inhibiting composition of claim 2, wherein said composition is arrived at, by stirring and heating said reaction mixture of claim 2, characterized in that said reaction mixture is heated to 160° C. under nitrogen gas purging, maintaining said reaction mixture between 160° C. to 180° C. for a period of 1 hour to 2 hours, raising temperature of said reaction mixture to from 185° C. to 250° C. and maintaining said reaction mixture with raised temperature for 1 to 24 hours, cooling the reaction mass to 100° C. and purging nitrogen gas into reaction vessel to drive out the hydrogen sulphide gas, thereby resulting into said composition.

4. A naphthenic acid corrosion inhibiting and sulphur corrosion inhibiting composition of claim 3, wherein said raising temperature of said reaction mixture varies from 190° C. to 230° C.

5. A naphthenic acid corrosion inhibiting and sulphur corrosion inhibiting composition of claim 3, wherein said raising temperature of said reaction mixture varies from 210° C. to 225 C.

6. A naphthenic acid corrosion inhibiting and sulphur corrosion inhibiting composition of claim 3, wherein said reaction mixture with raised temperature is maintained for 6 to 10 hours.

7. A composition of claim 1, wherein said olefin is an optionally substituted hydrocarbon group.

8. A composition of claim 7, wherein said olefin is an optionally substituted alkyl or alkenyl group.

9. A composition of claim 8, wherein said olefin is an optionally substituted branched alkyl or alkenyl group.

10. A composition of claim 9, wherein said olefin is a polyisobutenyl group.

11. A composition of claim 1, wherein said olefin has between 10 and 1000 carbon atoms.

12. A composition of claim 1, wherein said olefin has between 4 and 200 carbon atoms.

13. A composition of claim 1, wherein said olefin has a molecular weight of from 200 to 10,000.

14. A composition of claim 13, wherein olefin has a molecular weight of approximately 200 to approximately 1300.

15. A naphthenic acid corrosion inhibiting composition of claim 1, wherein said molar ratio of said olefin to said phosphorous pentasulphide is 1:1.

16. A process for high temperature naphthenic acid corrosion inhibition and /or sulphur corrosion inhibition of metallic surfaces of any of the hydrocarbon, wherein processing units of a petrochemical plant, with said processing units comprising distillation columns, strippers, trays, pumparound piping and related equipments, using the olefin phosphorous sulphur compound of claim 1, comprising the steps of:

a) heating the hydrocarbon containing naphthenic acid and /or sulphur compounds, to vapourize a portion of said hydrocarbon;

b) condensing a portion of the hydrocarbon vapours, passing through said hydrocarbon processing unit, to produce a condensed distillate;

c) adding to said distillate, before said condensed distillate is returned to said hydrocarbon processing unit or collected as a product, from 1 to 2000 ppm of said olefin phosphorous sulphur compound, in corrosion inhibition effective amount, capably forming a reaction mixture;

d) allowing said condensed distillate containing said olefin phosphorous sulphur compound, to contact said metallic surfaces of said hydrocarbon processing unit, to form a protective film on said surfaces whereby each surface is inhibited against corrosion; and e) allowing said condensed distillate to return to said hydrocarbon processing unit, or to be collected as said product.

17. A process, as claimed in claim 16, wherein said olefin of steps (c) and (d), comprises polyisobutylene, which is high reactive or normal.

18. A process according to claim 16, wherein said olefin phosphorous sulphur compound is arrived at, stirring and heating said reaction mixture of claim 1, characterized in that said reaction mixture is heated to 160° C. under nitrogen gas purging, maintaining said reaction mixture between 160° C. to 180° C. for a period of 1 hour to 2 hours, raising temperature of said reaction mixture to from 185° C. to 250° C. and maintaining said reaction mixture with raised temperature for 1 to 24 hours, cooling the reaction mass to 100° C. and purging nitrogen gas into reaction vessel to drive out the hydrogen sulphide gas, thereby resulting into said olefin phosphorous sulphur compound.

19. A process according to claim 18, wherein said raising temperature of said reaction mixture varies from 190° C. to 230° C.

20. A process according to claim 18, wherein said raising temperature of said reaction mixture varies from 210° C. to 225° C.

21. A process according to claim 18, wherein said reaction mixture with raised temperature is maintained for 6 to 10 hours.

22. A process according to claim 16, wherein said olefin is an optionally substituted hydrocarbon group.

23. A process according to claim 22, wherein said olefin is an optionally substituted alkyl or alkenyl group.

24. A process according to claim 23, wherein said olefin is an optionally substituted branched alkyl or alkenyl group.

25. A process according to claim 24, wherein said olefin is a polyisobutenyl group.

26. A process according to claim 16, wherein said olefin has between 4 and 1000 carbon atoms.

27. A process according to claim 16, wherein said olefin has a molecular weight of from 200 to 10,000.

28. A process according to claim 16, wherein said molar ratio of said olefin to said phosphorous pentasulphide is 1:1.

29. A method for producing naphthenic acid corrosion inhibiting composition comprising olefin phosphorous sulphur compound, wherein method comprises reacting olefin with phosphorous pentasulphide, characterized in that said olefin is reacted with phosphorous pentasulphide to form a reaction mixture comprising said olefin phosphorous sulphur compound, wherein the molar ratio of said olefin to said phosphorous pentasulphide is between 1:0.05 to 1:1.5, and
  wherein said reaction of the olefin with the phosphorous pentasulphide is carried out in multi-step heating and in presence of catalytic amount of sulphur, and under nitrogen gas purging, and thereby resulting into said composition.

30. A method of claim 29, wherein said olefin is polyisobutylene, which is high reactive or normal.

31. A method of claim 30, characterized in that said composition is arrived at, by stirring and heating said reaction mixture of claims 29, to 160° C. under nitrogen gas purging, maintaining said reaction mixture between 160° C. to 180° C. for a period of 1 hour to 2 hours, raising temperature of said reaction mixture to from 185° C. to 250° C. and maintaining said reaction mixture with raised temperature for 1 to 24 hours, cooling the reaction mass to 100° C. and purging nitrogen gas into reaction vessel to drive out the hydrogen sulphide gas, thereby resulting into said composition.

32. A method of claim 31, wherein said raising temperature of said reaction mixture varies from 190° C. to 230° C.

33. A method of claim 31, wherein said raising temperature of said reaction mixture varies from 210° C. to 225° C.

34. A method of claim 31, wherein said reaction mixture with raised temperature is maintained for 6 to 10 hours.

35. A method of claim 29, wherein said molar ratio of said olefin to said phosphorous pentasulphide is 1:1.

* * * * *

UNITED STATES PATENT AND TRADEMARK OFFICE
CERTIFICATE OF CORRECTION

PATENT NO. : 9,090,837 B2  
APPLICATION NO. : 12/593622  
DATED : July 28, 2015  
INVENTOR(S) : Mahesh Subramaniyam Page 1 of 1

It is certified that error appears in the above-identified patent and that said Letters Patent is hereby corrected as shown below:

Title page, item 73, the Assignee should read --DORF KETAL CHEMICALS (I) PRIVATE LIMITED, Mumbai (IN)--

Title page, item 56, the second reference should read --2,316,078 A *    4/1943 Loane et al.   ..........   508/354--

In the Claims

Claim 5, col. 17, line 49 replace "225 C." with --225° C.--

Claim 18, col. 18, line 38 replace "at, stirring" with --at, by stirring"

Claim 31, col. 20, line 3 replace "claims 29" with --claim 29--

Signed and Sealed this  
Twelfth Day of January, 2016

Michelle K. Lee  
*Director of the United States Patent and Trademark Office*